United States Patent [19]

McDermott

[11] 4,086,066

[45] Apr. 25, 1978

[54] METHOD FOR PREVENTING MICROORGANISM INDUCED CORROSION OF HYDROCARBON LIQUID STORAGE TANKS

[75] Inventor: Arthur R. McDermott, Houston, Tex.

[73] Assignee: Nalco Chemical Company, Oak Brook, Ill.

[21] Appl. No.: 770,887

[22] Filed: Feb. 22, 1977

[51] Int. Cl.² .............................................. C10L 1/32
[52] U.S. Cl. .......................................... 44/51; 44/67; 44/68; 206/524.7
[58] Field of Search .................. 206/524.7; 44/67, 68, 44/72, 51

[56] References Cited

U.S. PATENT DOCUMENTS

| | | | |
|---|---|---|---|
| 3,393,058 | 7/1968 | Oppermann | 44/68 |
| 3,892,905 | 7/1975 | Albert | 206/524.7 |

*Primary Examiner*—Allen B. Curtis
*Assistant Examiner*—Mrs. Y. Harris-Smith
*Attorney, Agent, or Firm*—John G. Premo; Robert A. Miller; Barry W. Sufrin

[57] ABSTRACT

Microorganism induced corrosion of storage vessels which contain a heel of water and an upper layer of hydrocarbon liquid may be prevented by adding to the hydrocarbon liquid contained in such storage vessels a water-dispersible polyvinyl alcohol package which contains a microbiocide.

6 Claims, No Drawings

METHOD FOR PREVENTING MICROORGANISM INDUCED CORROSION OF HYDROCARBON LIQUID STORAGE TANKS

INTRODUCTION

It is known that when petroleum-type hydrocarbon liquids are stored in large storage vessels such as storage tanks, fuel tanks of aircraft and holds of tankers, water invariably forms due to condensation or is initially present in the stored hydrocarbon liquid and slowly separates therefrom. This water gradually forms a reservoir or heel in the bottom of such storage containers. Since this water is relatively impure and its upper layer forms an interface with a liquid hydrocarbon, it is an excellent breeding ground for a wide variety of microorganisms. These microorganisms utilize the hydrocarbon liquid as a nutrient and multiply rapidly. The end result of this growth produces a corrosive environment which rapidly corrodes the ferrous metal container which contacts the hydrocarbon system. The corrosion is most severe along the interface between the oil and water.

An ancillary problem related to the growth of microorganisms in these systems is the production of unwanted sludge which tends to contaminate the stored oil.

This entire problem is discussed at great length in the specification of U.S. Pat. No. 3,393,058, the disclosure of which is incorporated herein by reference.

In order to combat the above problems, it is customary to treat the aqueous phase of these systems with a microbiocide. Since the heel or water phase of these systems is relatively small in comparison to the oil phase and is contained in the lower portion of the storage vessel, the treatment of the aqueous phase presents a difficult problem from a feeding standpoint. Since most storage containers are not provided with a feeding system to directly add a microbiocide to the aqueous layer, it is oftentimes necessary to add the microbiocide directly to the oil with the expectation that the biocide will reach the water in sufficient quantity to control the biological growth. In many cases, the most effective microorganism chemicals for combating this problem are soluble in hydrocarbon liquids. To overcome this mechanical feeding problem whereby the microbiocide is fed to the hydrocarbon liquid yet be allowed to concentrate in the aqueous phase, numerous solutions to the problem have been proposed.

One solution resides in admixing the microbiocides with other ingredients and then briquetting these ingredients to form various shapes which are added to the oil phase. These briquettes drop through the oil and rest in the water phase where they tend to slowly break up, thereby releasing the microbiocides. This approach, while working in some instances, is not entirely satisfactory since certain microorganism chemicals are liquid and are extremely difficult to formulate as solids.

It, therefore, becomes evident that if an improved method for feeding microorganism chemicals to hydrocarbon liquids stored in containers over a heel of water could be provided whereby microorganism induced corrosion would be reduced or eliminated, an advance in the art of treating these fluids would be afforded.

THE INVENTION

In accordance with the invention, it has been found that the microorganism induced corrosion of storage vessels which contain a small lower layer of water and a large upper layer of a hydrocarbon liquid may be reduced or eliminated by adding to the hydrocarbon liquid a water-dispersible polyvinyl alcohol package which contains a microorganism controlling amount of a microbiocide.

The Polyvinyl Alcohol Package

The polyvinyl alcohol used in preparing the packages used in the practice of the invention may be selected from a relatively large number of well known and commercially available grades of polyvinyl alcohol. The commercial polyvinyl alcohols have molecular weight ranges between 25,000 to as high as about 300,000. Their degree of hydrolysis ranges from about 75% up to as high as complete hydrolysis, e.g. about 99%. When it is desired to have a water-dispersible package, it is best to use either a low molecular weight polyvinyl alcohol, e.g., molecular weight about 25,000 - 35,000, or to use a higher molecular weight species, e.g., 170,000 - 300,000 M.W., which have a degree of hydrolysis not greater than about 95%. The water-dispersible characteristics of such polyvinyl alcohols, their properties and characteristics as well as the effect of certain well known plasticizers which may be optionally used in preparing the packages of the invention are described in detail in the book, *Water-Soluble Resins*, Second Edition, R. L. Davidson and Marshall Sittig, Van Nostrand Reinhold Company, 1968 (Chapt. 6), the disclosure of which is incorporated hereby by reference.

The polyvinyl alcohol package may be in the form of a pouch, bag, or any other shape which is capable of containing the microorganism control chemical. It is understood that for treating large storage vessels, the microorganism chemical might be fed to the system by using a number of small packages or pouches made of the polyvinyl alcohol packaging material. The thickness of the polyvinyl alcohol film used to prepare the package may vary from one sixteenth to several mills.

The microorganism control chemical is placed inside of the polyvinyl alcohol package and sealed. When added to the hydrocarbon liquid phase of the storage vessels, the polyvinyl alcohol is not affected by the hydrocarbon liquid. It, therefore, sinks through the oil phase and finally rests on the bottom of the tank in the water layer where the water dissolves or ruptures the package and releases the microbiocide to the water phase. Where the density of the microbiocide is such that it is near the specific gravity of the hydrocarbon liquid, it is contemplated that it would be combined with a weighting agent such as a boron or lead salt to allow the package to sink through the hydrocarbon liquid.

The Microbiocides

The types of microorganisms causing corrosion of the storage vessels vary and have not been systematically classified to any great extent. Typical microorganism oftentimes found associated with petroleum hydrocarbon liquids such as fuel oils, gasoline, jet fuel and the like are discussed in U.S. Pat. No. 3,393,058. It is fairly well known, however, that most of the organisms are anaerobic and may be adequately controlled using several well known biocides.

Typical of the microbiocides that may be used are methylene bis thiocyanate, tributyl tin oxide, 2-bromo-4' hydroxyacetophenone, various nickel compounds of the type described in U.S. 3,393,058, as well as many other well known commercially available microbiocides.

The nickel compositions useful in the invention may be chosen from a wide variety and a number of classes of specific nickel compounds. The nickel compositions should preferably be capable of releasing at least 0.5 ppm of nickel metal into the aqueous phase of the hydrocarbon fluid when added in use amounts, whether such aqueous phase exists in the form of a distinct bottom layer or as droplets dispersed throughout the petroleum. Greatly preferred nickel substances usually exist in partial or complete ionic form in the aqueous phase, and the nickel itself is thereby immediately available in ionized form to act upon the microbes contained therein. As an adjunct of this then, it is preferred that the inorganic, or organic nickel compositions have sufficient solubility in water to furnish at least microbiocidal amounts of nickel to the aqueous phase of the hydrocarbon fluid. As also mentioned above, it has been determined that biocidal activity is generally present when the nickel composition, regardless of its structural composition, is present in sufficient amounts in the aqueous phase to donate thereto at least 0.5 ppm of nickel. Preferred nickel compositions then are those which have some solubility or dispersibility in water, even if such characteristic is only to the extent of the aforementioned use amounts of the nickel additive. The most preferred nickel compositions have the property of donating at least 1 ppm of nickel to the oil-water system when the nickel composition itself is added in at least an amount of 2.0 ppm.

The nickel composition as furnished to the hydrocarbon fluid may exist in a wide variety of forms, organic and inorganic. These may be in form of organic or inorganic salts, as covalent organo-nickel compounds, as nickel metal complexes of organics, etc.

Preferred among the nickel compositions which may be employed in practice of the invention, are two broad classes. First are inorganic nickel compounds, which are generally water soluble in nature. Among those nost useful are nickel halides, nitrates, sulfates, etc.

Another extremely useful class of compounds are nickel complexes of organic compounds which contain at least one basic nitrogen group. Such complexes are easily formed by reaction of any inorganic nickel compound and the specific organic amine to be thereby complexed. Such amine reactants may include alkylene polyamines; polyalkylene polyamines; primary, secondary and tertiary monoamines such as dimethylamine, trimethylamine, ethylamine, butylamines, N-ethylbutylamine, etc.; arylamines such as aniline and substituted anilines; heterocyclic amines such as ethylene imine, morpholine, etc.; cyclic amines such as cyclohexylamine; alkaryl amines such as dodecyl aniline; fatty amines such as $C_2C_{22}$N-substituted primary, secondary and tertiary amines and polyamines; amino acids such as glycine; imidazolines and substituted imidazolines, etc. As mentioned above, these amine complexes are easily prepared by merely stirring together a source of nickel, such as an inorganic salt, with the amine in any desired ratio. The complexing reaction may be run with or without heat application.

Other nickel complexes such as ketonates, hydroxy carboxylates, citrates, tartarates, certain Schiff's bases and the like may also be used. A particularly useful microbiocide for treating the systems of the type described is a blend of methylene bis thiocyanate and tributyl tin oxide combined in weight ratios varying from 1:20 to 20:1. Most of these biocides have a relatively high degree of oil solubility and if directly added to the oil, would, of course, be dissolved therein, thereby diminishing their activity to a substantial degree.

In many instances, the microbiocides are formulated in hydrocarbon liquids as solutions. Such formulas may be packaged in polyvinyl alcohol containers which are impervious to hydrocarbon liquids.

EXAMPLE

A typical product of the invention would be a small, 1-mill thick, pouch-like polyvinyl alcohol which contained No. 2 fuel oil which had dissolved therein 2% by weight of methylene bis thiocyanate. This material would be placed in the package and then sealed. If this type of product were to be used to treat a large storage tank, enough pouches would be added to the hydrocarbon liquid to provide about 2 ppm of the methylene bis thiocyanate to the water phase. The packages could be added initially on a slug basis and then additional packages added from time to time to maintain microorganism control in the system.

Having thus described my invention, it is claimed as follows:

1. A method for preventing microorganism induced corrosion of a storage vessel which contains a small lower layer of water and a large upper layer of a hydrocarbon liquid by introducing a microorganism control chemical into the small lower layer of water which comprises:
    (A) placing the microorganism control chemical inside a polyvinyl alcohol package;
    (B) sealing the polyvinyl alcohol package;
    (C) dropping the polyvinyl alcohol package into the storage vessel so that it can penetrate the large upper layer of hydrocarbon liquid and pass into the small lower layer of water; and,
    (D) permitting the polyvinyl alcohol package to dissolve in the water thereby releasing the microorganism control chemical.

2. The method of claim 1 wherein a weighting agent is placed in the polyvinyl alcohol package along with the microorganism control chemical in order to make the package sink through the large upper layer of hydrocarbon liquid to the small lower layer of water.

3. The method of claim 1 where the microbiocide is methylene bis thiocyanate.

4. The method of claim 1 where the microbiocide is a mixture of tributyl tin oxide and methylene bis thiocyanate.

5. The method of claim 1 where the microbiocide is a nickel compound.

6. The method of claim 1 where the microbiocide is tributyl tin oxide.

* * * * *

UNITED STATES PATENT AND TRADEMARK OFFICE
CERTIFICATE OF CORRECTION

PATENT NO. : 4,086,066
DATED : April 25, 1978
INVENTOR(S) : Arthur R. McDermott

It is certified that error appears in the above-identified patent and that said Letters Patent are hereby corrected as shown below:

Please insert on the first page of the patent:

© 1978, Nalco Chemical Company

Signed and Sealed this

Fourteenth Day of November 1978

[SEAL]

Attest:

RUTH C. MASON
Attesting Officer

DONALD W. BANNER
Commissioner of Patents and Trademarks